United States Patent
Howlett

[11] Patent Number: 6,062,214
[45] Date of Patent: May 16, 2000

[54] INHALER FOR MEDICAMENT

[75] Inventor: David Howlett, Norfolk, United Kingdom

[73] Assignee: Bespak plc, United Kingdom

[21] Appl. No.: 08/959,447

[22] Filed: Oct. 28, 1997

[30] Foreign Application Priority Data

Oct. 30, 1996 [GB] United Kingdom ................... 9622546

[51] Int. Cl.[7] ........................... A61M 11/00; A61M 15/00
[52] U.S. Cl. ............................... 128/200.23; 128/203.15; 128/200.14; 128/200.18
[58] Field of Search ........................ 128/200.23, 203.15, 128/203.12, 200.14, 200.18, 200.21, 205.11, 206.29; 239/296

[56] References Cited

U.S. PATENT DOCUMENTS

| | | | |
|---|---|---|---|
| 3,658,059 | 4/1972 | Steil | 128/173 R |
| 4,534,343 | 8/1985 | Nowacki | 128/200.23 |
| 4,907,583 | 3/1990 | Wetterlin et al. | 128/203.15 |
| 5,033,463 | 7/1991 | Cocozza | 128/203.15 |
| 5,113,855 | 5/1992 | Newhouse | 128/203.15 |
| 5,161,524 | 11/1992 | Evans | 128/203.15 |
| 5,165,391 | 11/1992 | Chiesi et al. | 128/200.23 |
| 5,309,900 | 5/1994 | Knoch et al. | 128/200.14 |
| 5,415,162 | 5/1995 | Casper et al. | 128/203.12 |
| 5,435,297 | 7/1995 | Klein . | |
| 5,458,135 | 10/1995 | Patton et al. | 128/200.14 |
| 5,615,670 | 4/1997 | Rhodes | 128/203.15 |
| 5,678,538 | 10/1997 | Drought | 128/203.15 |
| 5,740,794 | 4/1998 | Smith et al. | 128/203.15 |
| 5,785,049 | 7/1998 | Smith et al. | 128/203.15 |

FOREIGN PATENT DOCUMENTS

| | | |
|---|---|---|
| 2279879 | 1/1995 | United Kingdom . |
| WO 92/20391 | 11/1992 | WIPO . |

*Primary Examiner*—Aaron J. Lewis
*Assistant Examiner*—Todd Martin
*Attorney, Agent, or Firm*—Smith, Gambrell & Russell

[57] ABSTRACT

The invention relates to inhaler products, such as medicaments, and particularly to an inhaler for transferring to a patient a metered dose of medicament contained in a pressurized dispensing container. The inhaler includes a housing for receiving a pressurized dispensing container of medicament and a mouthpiece for insertion into the mouth or a user of the inhaler. An outlet in the housing communicates with the mouth piece via a duct ending in an outlet. At least one air inlet is provided for allowing air into the inhaler. The air inlet(s) being positioned downstream relative to the duct outlet. A restricted airflow passage is provided between the air inlet(s) and a location adjacent to the outlet of the duct. The inhaler also includes a vortex generating arrangement positioned in the restricted airflow passage, such that, in use, when a user inhales through the mouthpiece, a swirling airflow is created from the inlet(s) to the mouthpiece along the passage towards the duct outlet. The swirling airflow exits the restricted airflow passage to create a swirling airflow in the neck region of the duct outlet that swirls about a central axis of the duct outlet and the swirling airflow has a component directed in reverse to the airflow form the duct outlet of the mouthpiece for reducing the velocity of medicament dispensed from the pressurized dispensing container via the duct and duct outlet.

11 Claims, 6 Drawing Sheets

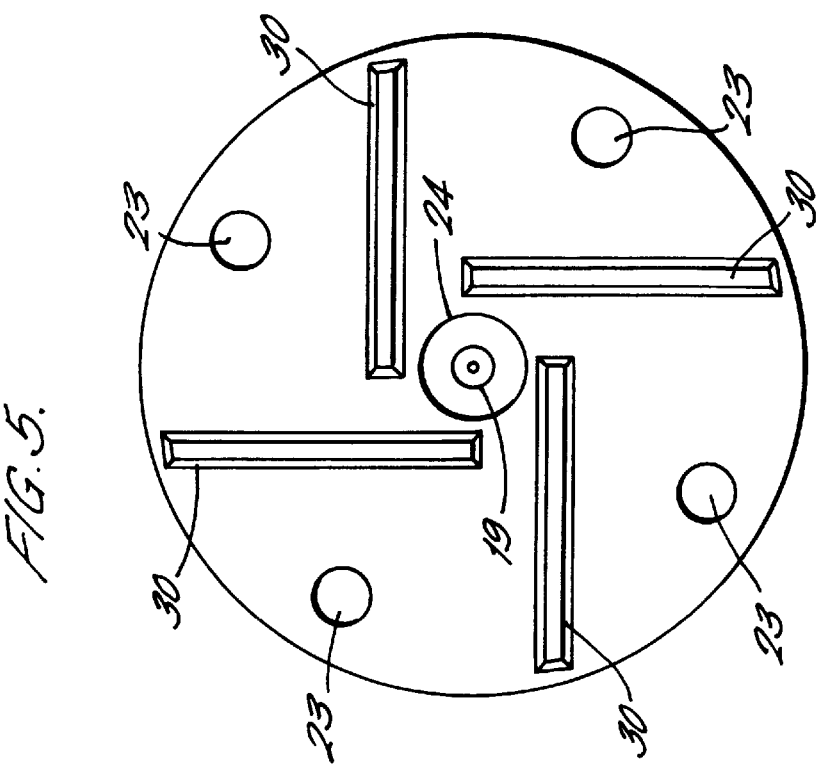
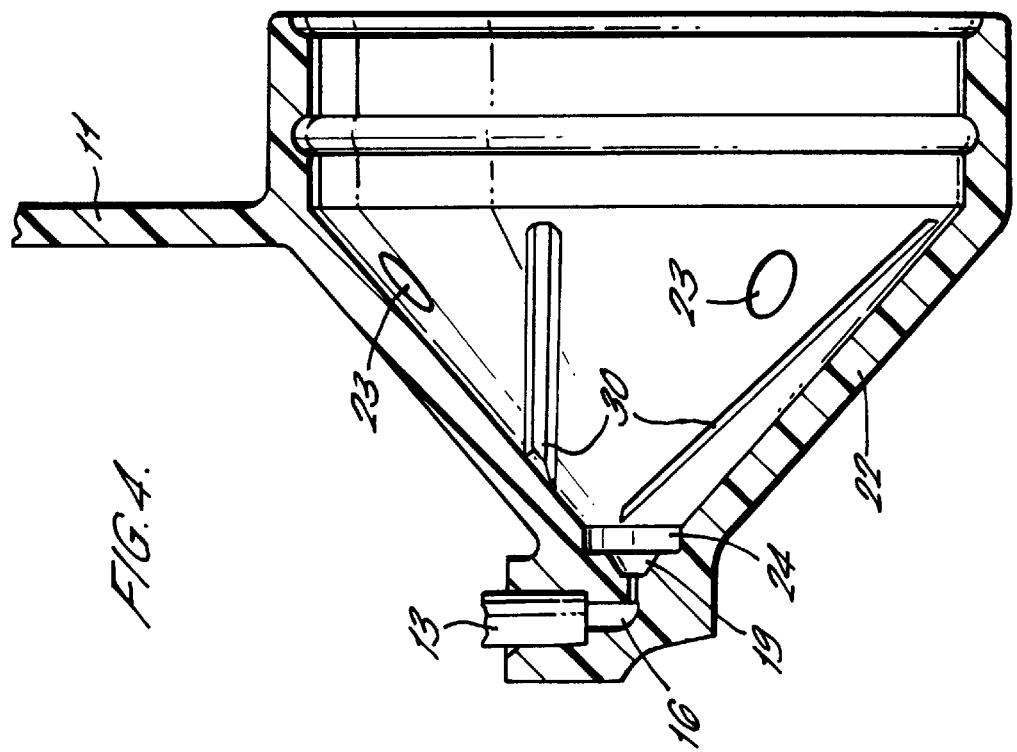

INHALER FOR MEDICAMENT

FIELD OF THE INVENTION

The invention relates to an inhaler for products such as medicaments and particularly to an inhaler for transferring to a patient a metered dose of medicament contained in a pressurised dispensing container.

BACKGROUND OF THE INVENTION

In known metered dose inhalers, the aerosol stream from a pressurised dispensing container is fired towards a patient or user of the inhaler into an air flow travelling in the same direction. In known devices, a user inhales through a mouth piece of the inhaler and creates an air flow through the container from air inlet holes which are generally at a part of the inhaler well spaced from the mouth piece. The medicament is then released into this air flow at a point between the air inlet holes and the mouth piece so that it is travelling in the same direction as the air flow. Typically in such devices, there is no restriction in the air flow between the air inlet holes and the mouth piece. Because of this, a substantial air flow may be created by a user of the device and, because the medicament is fired into the air flow in the same direction as the air flow, the effect is that particles of medicament can attain quite substantial velocities. As inhalers of this type are normally designed to be as small as practical for the convenience of users, the distance between the point at which the medicament is fired into the air flow and the patients mouth is usually quite small so that there is little distance to reduce the inertia of the particles of medicament with the result that the particles may impact in the oro-pharynx of a user with quite high velocity. This can be a problem with some medicaments.

In an effort to overcome this problem, devices have been produced in which the medicament is fired into a holding volume which allows the velocity of the medicament to be reduced and also allows some evaporation to occur.

U.S. Pat. No. 5,435,297 discloses a medical device for inhaling a metered aerosol comprising a cylindrical housing with a receiving chamber and first main air channels extending axially within the housing. A mouthpiece is co-axially connected to the housing. An atomising and vortexing chamber is delimited by the housing and the mouthpiece. Second main air channels extend within the mouthpiece and communicate with the first main air channels. Branch air channels extend at a slant to an axial direction within a partition positioned between the receiving chamber and the atomising and vortexing chamber. The branch air channels are connected to the first main air channels and open into the atomising and vortexing chamber. Inhaled airflow through the branch channels aids the atomisation of the aerosol. However, the branch channels do not slow the velocity of the dispensed medicament. Rather, they tend to increase the velocity of the medicament particles.

Devices such as those disclosed in U.S. Pat. No. 5,435,297, with a holding volume tend to be of significantly larger size than the standard metered dose inhalers and therefore less convenient and attractive to users.

One solution proposed in GB-A-2279879 uses a reverse flow. In this inhaler the air inlets are provided at a location axially between the air outlet of the duct means connecting an outlet of the container with the mouth piece and the mouth piece, and a passage is provided connecting the inlets to a location adjacent the outlet of the duct means. Thus when a user inhales through the mouth piece, an air flow is created from the inlet means to the mouth piece, the air flow having a component directed away from the mouth piece towards the outlet of the duct means.

SUMMARY OF THE INVENTION

The present invention seeks to provide an inhaler which allows delivery of medicament to a user at reduced velocity without significantly increasing the size of the inhaler.

The invention therefore provides an inhaler for medicament comprising a housing adapted to receive a pressurised dispensing container of medicament, a mouth piece for insertion into the mouth of a user of the inhaler, duct means connecting an outlet of the container with the mouth piece and air inlet means for allowing air into the inhaler when a user applies suction to the mouth piece in which the air inlet means are provided at a location axially between the air outlet of the duct means and the mouth piece, and passage means are provided connecting the inlet means to a location adjacent the outlet of the duct means, further comprising vortex generating means in the passage means so that, in use, when a user inhales through the mouth piece, a swirling air flow is created from the inlet means to the mouth piece.

BRIEF DESCRIPTION OF THE DRAWINGS

Preferred embodiments of the present invention will now be described, by way of example only, with reference to the accompanying drawings, in which:

FIG. 4 is a side elevation of a section of an inhaler according to the present invention for receiving a mouth piece illustrating the vortex generator which is the same as that in FIG. 1 but with air holes formed on a sloping section of the housing;

FIG. 5 is an end view of the frusto-conical portion of the housing section of FIG. 4;

DETAILED DESCRIPTION OF THE PREFERRED EMBODIMENTS

Figure 1:
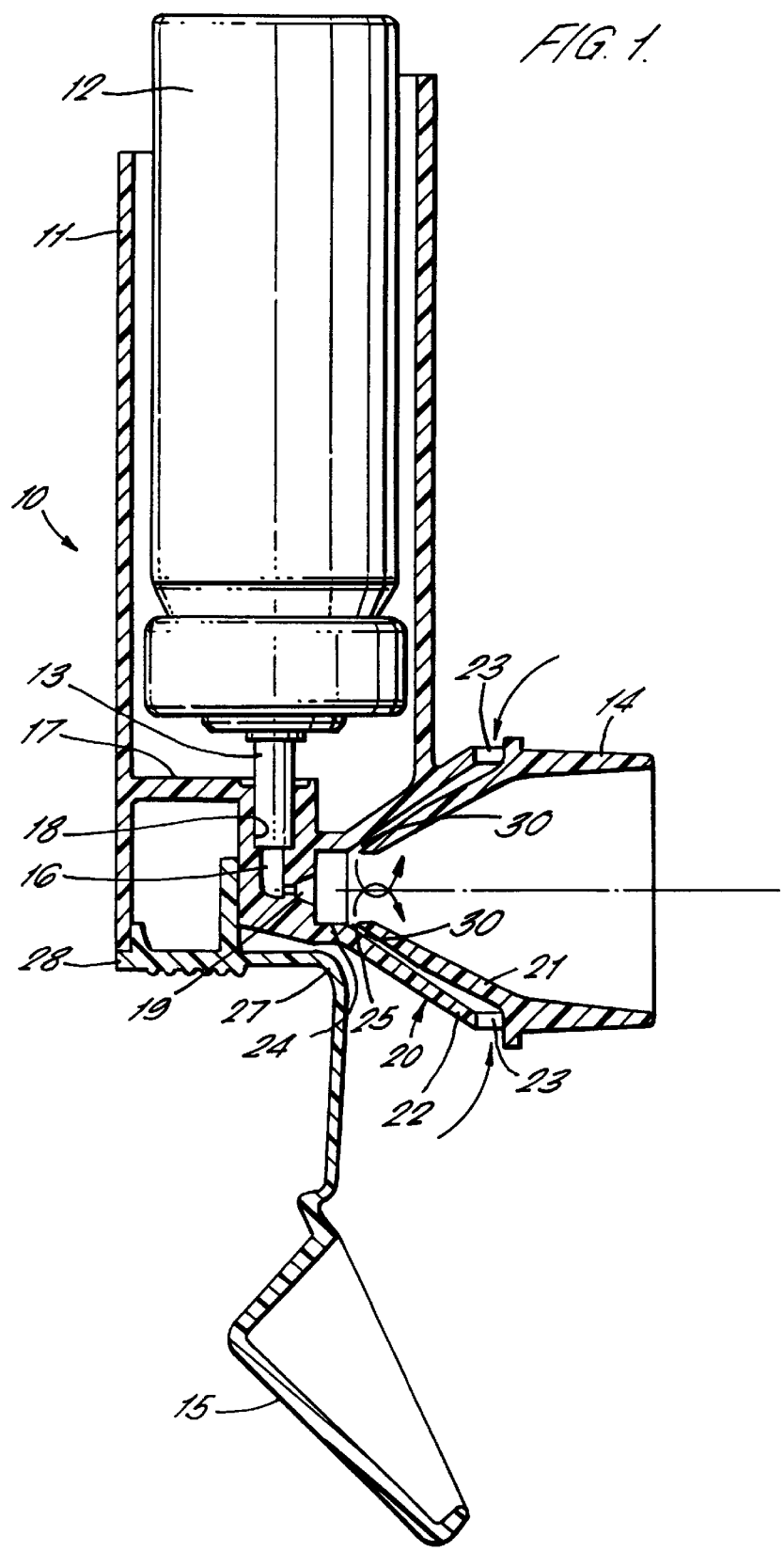
FIG. 1 is a cross-sectional side elevation of an inhaler according to the present invention.

FIG. 1 provides a cross-sectional view of one embodiment of an inhaler 10 according to the present invention.

Referring to FIG. 1, an actuator or inhaler 10 for a product such as a medicament, comprises a housing 11 for receiving a pressurised dispensing container 12 of medicament, a mouth piece 14 for insertion into the mouth of a user of the inhaler 10 and a cover 15 for the mouth piece 14.

The container housing 11 is generally cylindrical and open at its upper end. A lower wall 17 of the housing 11 includes a socket 18 defining a seat for receiving the tubular valve stem 13 of the container 12. The socket 18 communicates, via a duct 16 ending in an orifice 19, with the mouth piece 14.

The mouth piece 14, which may be generally circular or shaped to fit the mouth, is connected to the housing 11 through a generally frusto-conical wall portion 20. The wall portion 20 includes inner and outer walls 21, 22, the inner wall 21 being an extension of the mouth piece 14. The outer wall 22 forms, with the inner wall 21, a restricted air flow passage from inlet air holes 23 provided in the outer wall 22 around the periphery of the mouth piece 14 to a restricted air inlet 25 adjacent a neck portion 24 of the device 10. On the inner surface of outer wall 22 are formed means for generating a vortex (i.e., the inhaler includes a vortex generator). An example of a preferred vortex generator can be seen in FIG. 1 (and in greater detail) in FIGS. 4 and 5 comprises four raised vanes 30 located around the inner surface of the outer wall 22 at an angle of incidence to the air flow. When the mouth piece 14 is fitted in the housing 11, the inner wall 21 seals against the top surfaces of the vanes 30 and forms the above noted restricted airflow passage.

The cover 15 of the device 10 which fits over the open mouth piece 14 is connected by a flexible hinge portion 27 to a cover attachment 28 which fits in the lower part of the housing 11 to attach the cover 15 to the housing 11. All of the components of the inhaler 10 may be plastics mouldings.

It will be appreciated that the lower wall formation 17 of housing 11 forms a barrier between the open end of the housing 11 and the mouth piece 14 so that there is no air flow passage from around the container 12, or the left side of the housing 11 (as viewed in the drawing), to the mouth piece 14.

In use of the inhaler 10, a patient or user holds the inhaler 10, usually in one hand, and applies his mouth to the mouth piece 14. The user then inhales through the mouth piece 14 and this creates an air flow from inlet air holes 23 along the channels created between the vanes 30, and the inner and outer walls 21, 22, via the restricted air inlet 25 to the mouth piece 14. It will be appreciated that the inlet air holes 23 are arranged downstream of the orifices 19 relative to the mouth piece 14, that is to say the inlet air holes 23 are axially closer to the mouth piece 14 than the neck portion 24 and orifice 19. This ensures that when a user inhales through the mouth piece 14, the air flow is not directly from a position upstream of the orifice 19 to the mouth piece 14 but has at least a component of reverse flow towards the orifice 19. The effect of the reverse air flow and vortex generator 30 is to create a swirling air flow in the neck portion 24. After the user has started inhaling through the mouth piece 14, the container 12 is depressed downwardly on to its stem 13 to release a dose of medicament from the container. The dose of medicament is projected by the pressure in the container 12 through the orifice 19 and then mixes with the swirling air flow in the neck portion 24 and thence is inhaled by the user.

Figure 2:
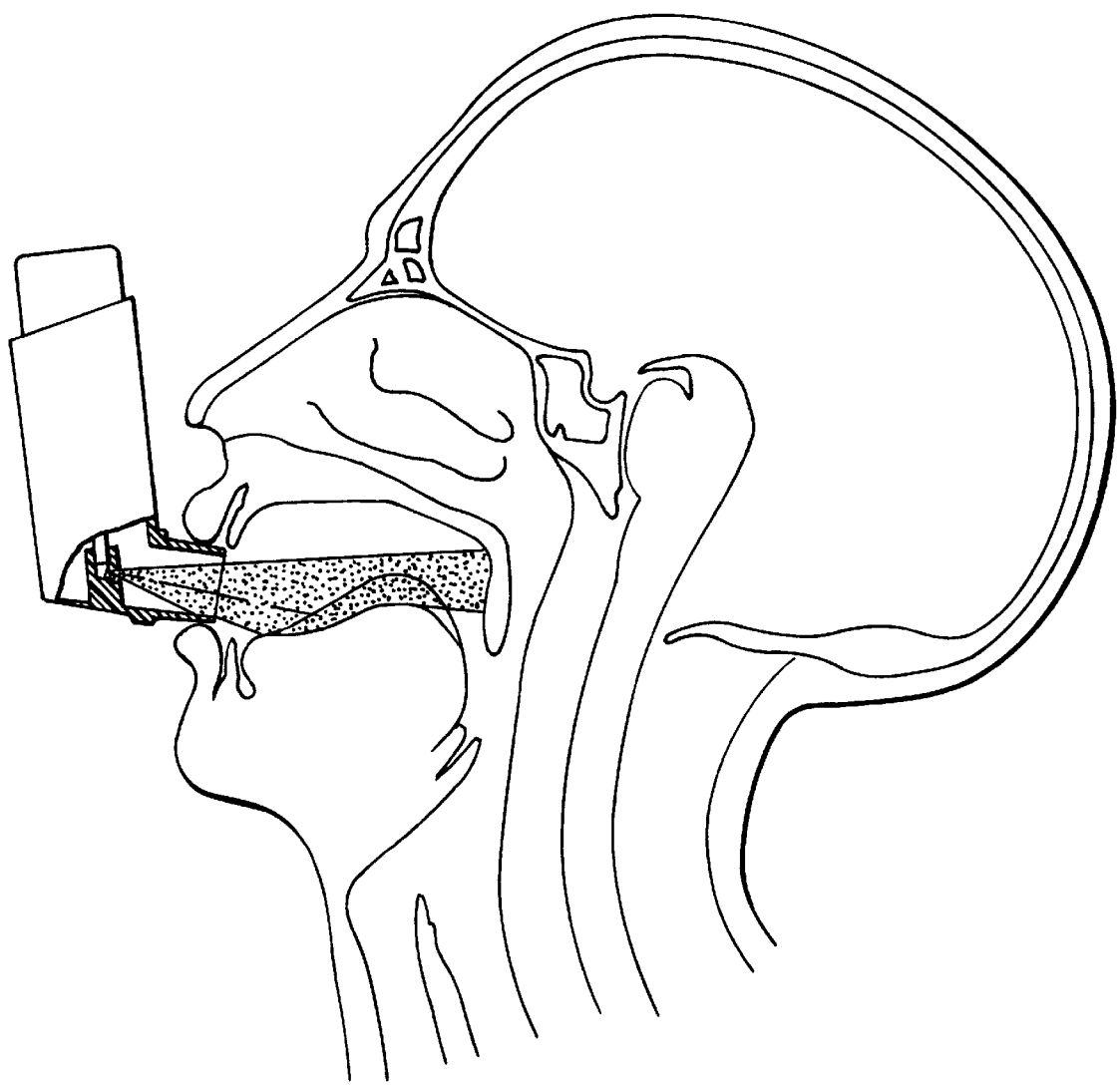
FIG. 2 is a schematic representation showing a prior art inhaler in use illustrating the spray pattern within the mouth and throat of the user.
Figure 3:
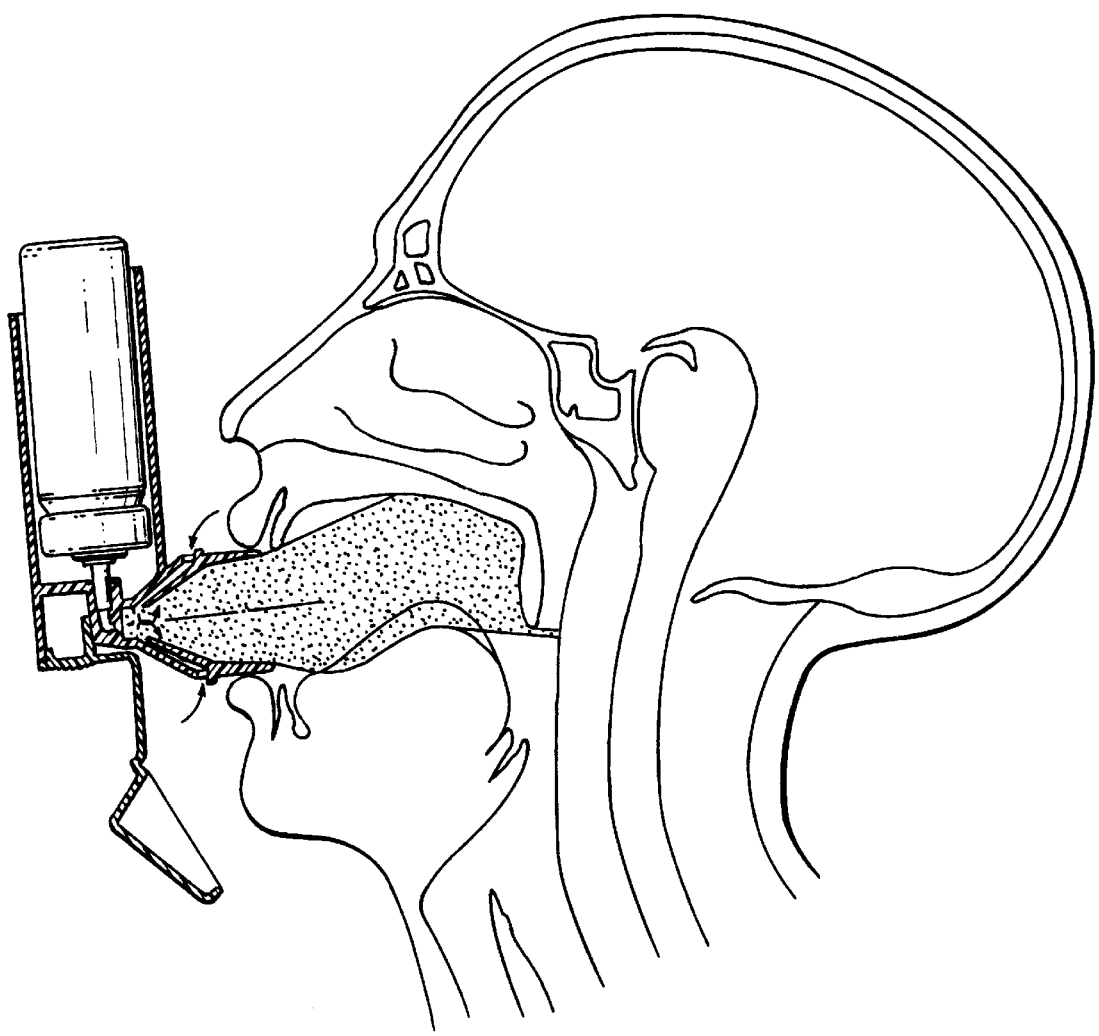
FIG. 3 is a schematic representation similar to that of FIG. 2 showing the inhaler of FIG. 1 in use.
Figure 7:
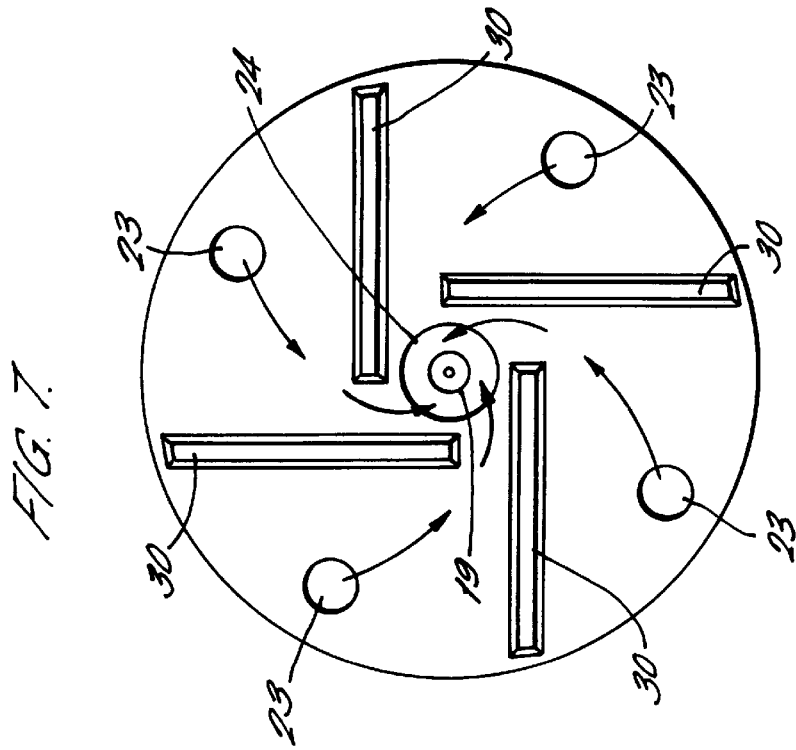
FIG. 7 is an end view of the frusto-conical portion of the housing section of FIG. 4 showing the direction of air flow.
Figure 6:
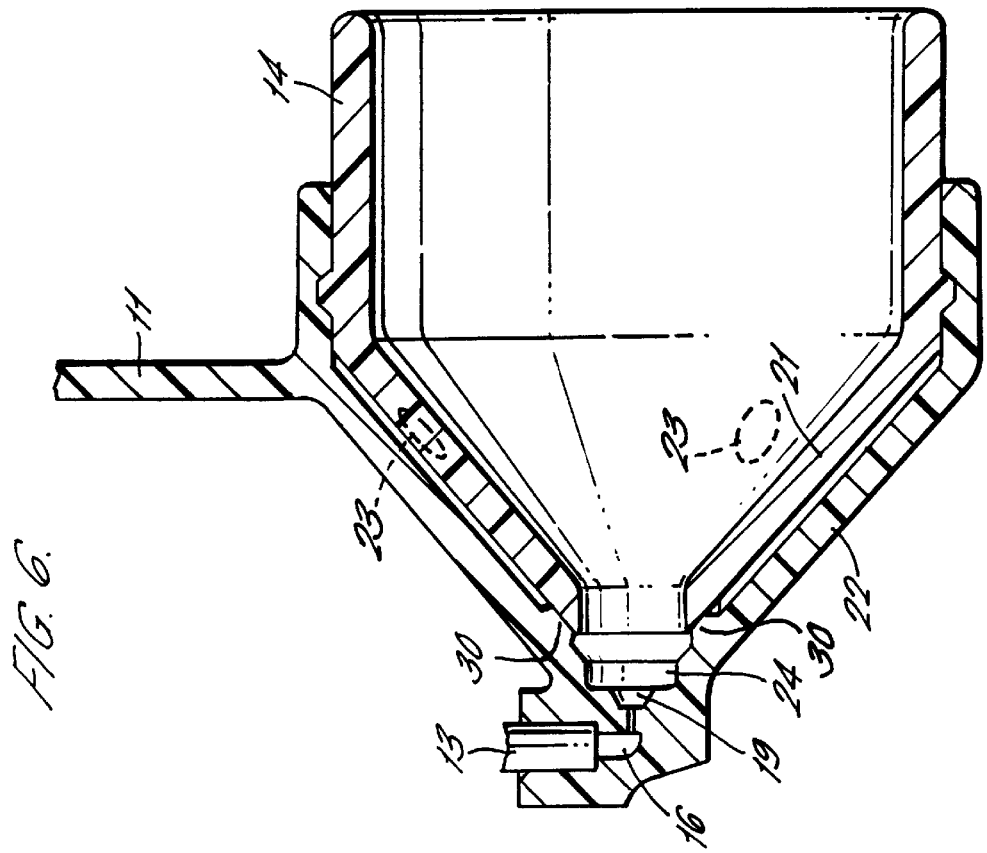
FIG. 6 is a cross-sectional side elevation of the section of housing of FIG. 4 with the mouth piece fitted.

The reverse flow component of air flow and the vortex created by the vortex generator ensure that the velocity of medicament particles is relatively low when they enter the oro-pharynx region of the patient. The spray pattern formed during use of a prior art inhaler is shown in FIG. 2. This spray is a high velocity, narrow cone, downwardly angled spray shown by the shaded envelope. The spray pattern formed during use of the inhaler of the present invention is illustrated in FIG. 3. The spray pattern is much wider and more upwardly angled as the product is dispersed with a greater volume of air. Thus the inhaler 10 is more effective and more comfortable to use.

When not in use, the cover 15 is placed over the mouth piece 14 in the and when the inhaler is to be used, the cover is removed by hinging it away from the mouth piece 14.

Figure 9:
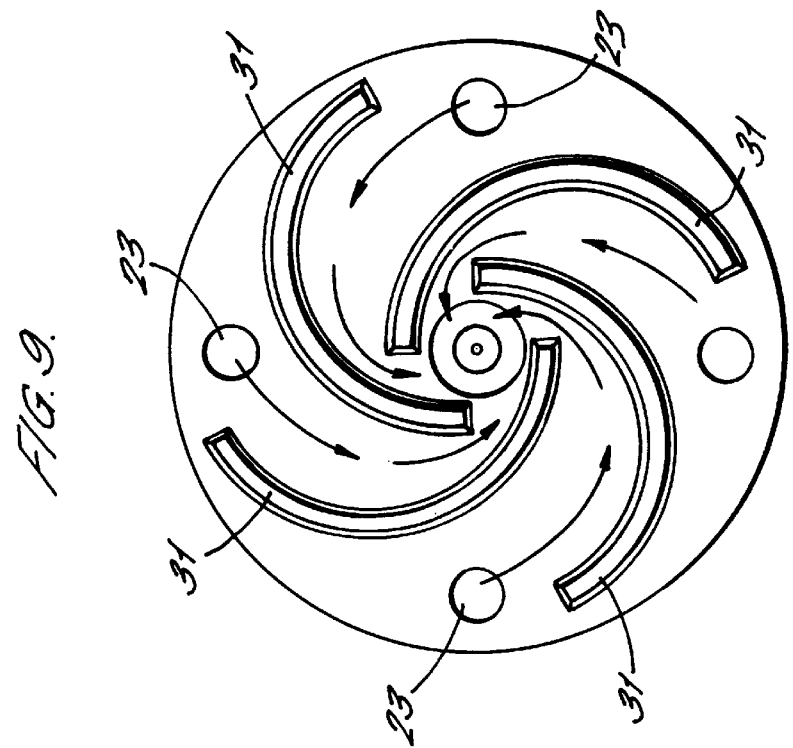
FIGS. 8 and 9 correspond to FIGS. 6 and 7 and illustrate an alternative vortex generator.
Figure 8:
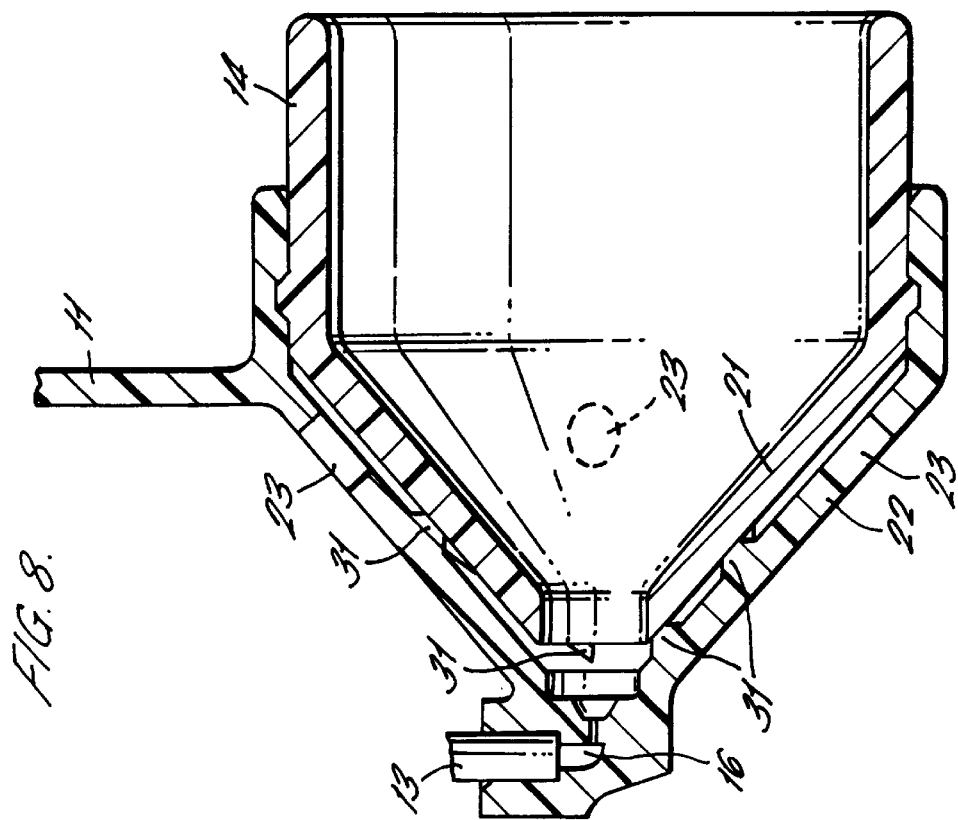

An alternative construction of vortex generator for use in the present invention is illustrated in FIGS. 8 and 9. In this arrangement the vanes 31 are curved.

Although only four vanes are shown in the foregoing embodiments, other numbers of vanes can be used which provide sufficient swirl to the air flow.

What is claimed is:

1. An inhaler for medicament comprising a housing for receiving a pressurized dispensing container of medicament, a mouthpiece for insertion into the mouth of a user of an inhaler, an outlet in the housing communicating with the mouthpiece via a duct ending in a duct outlet, at least one air inlet for allowing air into the inhaler, the said at least one air inlet being positioned downstream relative to the duct outlet, and a restricted airflow passage being provided between the said at least one air inlet and a location adjacent to the outlet of the duct, further comprising a vortex generator in the restricted airflow passage, such that, in use, when a user inhales through the mouthpiece, a swirling airflow is created from the said at least one air inlet to the mouthpiece along the passage towards the duct outlet, the swirling airflow having a component directed in reverse to the direction of medicament dispensed from the duct outlet of the mouthpiece for reducing the velocity of medicament dispensed from a pressurized dispensing container via the duct and duct outlet.

2. An inhaler as claimed in claim 1 in which the vortex generating means comprise a plurality of raised vanes in the restricted airflow passage at an angle of incidence to the air flow.

3. An inhaler as claimed in claim 1 in which the restricted airflow passage is formed between a wall of the housing and the mouthpiece, and the vortex generator is located on the wall of said housing.

4. An inhaler as claimed in claim 2 in which the vanes are straight sided.

5. An inhaler as claimed in claim 2 in which the vanes are curved.

6. An inhaler as claimed in claim 3 wherein said mouthpiece is a separate unit that is fittable within a reception cavity of said housing such that a wall of said mouthpiece seals against top, contact surfaces of said vanes.

7. An inhaler as claimed in claim 6 wherein said reception cavity is frusto-conical in shape.

8. An inhaler for medicament comprising a housing for receiving a pressurized dispensing container of medicament, a mouthpiece for insertion into the mouth of a user of an inhaler, an outlet in the housing communicating with the mouthpiece via a duct ending in a duct outlet, at least one air inlet for allowing air into the inhaler, said at least one air inlet being positioned downstream relative to the duct outlet, and a restricted airflow passage being provided between said at least one air inlet and a location adjacent to the outlet of the duct, said inhaler further comprising a plurality of vortex vanes positioned in the restricted airflow passage, such that, in use, when a user inhales through the mouthpiece, a swirling airflow is created from the said at least one air inlet to the mouthpiece along the passage towards the duct outlet, with the swirling airflow exiting said restricted passageway for mixing at the duct outlet with medicament dispensed from a pressurized dispensing container, and with the swirling airflow having a component directed in reverse to the direction of medicament dispensed from the pressurized dispensing container via the duct and the duct outlet so as to reduce the velocity of medicament being dispensed through said duct oulet.

9. An inhaler as claimed in claim 8, in which the restricted airflow passage is formed between a wall of the housing and the mouthpiece and the vanes are positioned between the wall of said housing and the mouthpiece.

10. An inhaler as claimed in claim 8 wherein said mouthpiece is a separate unit that is fittable within a reception cavity of said housing such that a wall of said mouthpiece seals against top, contact surfaces of said vanes.

11. An inhaler as claimed in claim 10 wherein said reception cavity is frusto-conical in shape.

* * * * *